US010898168B2

(12) United States Patent
Shepard et al.

(10) Patent No.: US 10,898,168 B2
(45) Date of Patent: Jan. 26, 2021

(54) MICRON-SCALE ULTRASOUND IDENTIFICATION SENSING TAGS

(71) Applicant: THE TRUSTEES OF COLUMBIA UNIVERSITY IN THE CITY OF NEW YORK, New York, NY (US)

(72) Inventors: Kenneth L. Shepard, Ossining, NY (US); Hongki Kang, South Korea (KR); Jordan Thimot, New York, NY (US); Chen Shi, New York, NY (US)

(73) Assignee: The Trustees of Columbia University in the city of New York, New York, NY (US)

( * ) Notice: Subject to any disclaimer, the term of this patent is extended or adjusted under 35 U.S.C. 154(b) by 0 days.

(21) Appl. No.: 15/911,973

(22) Filed: Mar. 5, 2018

(65) Prior Publication Data

US 2018/0193000 A1     Jul. 12, 2018

Related U.S. Application Data

(63) Continuation of application No. PCT/US2016/050165, filed on Sep. 2, 2016.
(Continued)

(51) Int. Cl.
*H04B 11/00*     (2006.01)
*A61B 8/00*     (2006.01)
(Continued)

(52) U.S. Cl.
CPC .................. *A61B 8/56* (2013.01); *A61B 8/12* (2013.01); *A61B 8/4427* (2013.01); *A61B 8/469* (2013.01);
(Continued)

(58) Field of Classification Search
CPC .......... A61B 8/56; A61B 8/469; A61B 8/523; A61B 8/12; A61B 8/4427; G01S 7/52036;
(Continued)

(56) References Cited

U.S. PATENT DOCUMENTS 5,423,334 A * 6/1995 Jordan ................. G06K 7/0008
                                                                                128/899
6,447,448 B1    9/2002   Ishikawa et al.
(Continued)

FOREIGN PATENT DOCUMENTS

CN          205306997 U      6/2016

OTHER PUBLICATIONS

Akin et al., "A Wireless Implantable Multichannel Digital Neural Recording System for a Micromachined Sieve Electrode," IEEE Journal of Solid-State Circuits, 33(1):109-118 (1998).
(Continued)

*Primary Examiner* — Charles D Garber
*Assistant Examiner* — S M Sohel Imtiaz
(74) *Attorney, Agent, or Firm* — Hunton Andrews Kurth LLP (57) ABSTRACT

Apparatus and methods for powering micron-scale implantable and injectable integrated circuit (IC) chips for in-vivo sensing and acquisition of various physiological signals are provided. The disclosed subject matter includes the integration of piezoelectric transducers, such as polyvinylidene fluoride (PVDF) or lead zirconate titanate (PZT), onto implantable and injectable IC chips for power transfer and data transmission using ultrasound waves generated from commercial ultrasound imaging equipment.

18 Claims, 8 Drawing Sheets

Related U.S. Application Data (60) Provisional application No. 62/214,822, filed on Sep. 4, 2015.

(51) Int. Cl.
    *A61B 8/12*         (2006.01)
    *A61B 8/08*         (2006.01)
    *G01S 7/52*         (2006.01)
    *G10K 11/34*       (2006.01)
    *H01L 27/146*     (2006.01)

(52) U.S. Cl.
CPC .......... *A61B 8/523* (2013.01); *G01S 7/52036* (2013.01); *G01S 7/52082* (2013.01); *G10K 11/343* (2013.01); *H01L 27/14601* (2013.01); *H04B 11/00* (2013.01)

(58) Field of Classification Search
CPC .............. G01S 7/52082; G10K 11/343; H01L 27/14601; H04B 11/00
See application file for complete search history.

(56) References Cited

U.S. PATENT DOCUMENTS

| | | | |
|---|---|---|---|
| 6,539,253 | B2 | 3/2003 | Thompson et al. |
| 7,904,160 | B2 | 3/2011 | Brodnick et al. |
| 8,108,048 | B2 | 1/2012 | Masoud |
| 8,183,745 | B2 | 5/2012 | Trolier-mckinstry et al. |
| 8,292,834 | B2 | 10/2012 | El-bialy et al. |
| 8,591,419 | B2 | 11/2013 | Tyler |
| 8,764,677 | B2 | 7/2014 | Toumazou et al. |
| 8,824,161 | B2 | 9/2014 | Askarinya et al. |
| 9,079,137 | B2 | 7/2015 | Sim et al. |
| 2003/0111669 | A1* | 6/2003 | Lin ........................ H03K 3/011 257/143 |
| 2007/0046369 | A1* | 3/2007 | Schober ............. G06K 19/0713 330/7 |
| 2008/0238630 | A1* | 10/2008 | Chen .................. G08B 13/2417 340/10.5 |
| 2009/0057414 | A1* | 3/2009 | Brunet ............. G06K 19/07749 235/492 |
| 2010/0004523 | A1* | 1/2010 | August ................ A61B 5/0031 600/365 |
| 2011/0009734 | A1 | 1/2011 | Foley et al. |
| 2011/0034912 | A1* | 2/2011 | de Graff ........... H01L 27/14687 606/21 |
| 2011/0178578 | A1* | 7/2011 | Porat .................... A61K 9/0009 607/60 |
| 2011/0188337 | A1* | 8/2011 | Rathgeber ........... B01F 11/0266 366/108 |
| 2011/0237953 | A1 | 9/2011 | Olsson et al. |
| 2012/0041310 | A1* | 2/2012 | Towe ....................... A61B 5/68 600/437 |
| 2013/0043768 | A1 | 2/2013 | Cochran et al. |
| 2014/0058292 | A1 | 2/2014 | Alford et al. |
| 2014/0176066 | A1 | 6/2014 | Dronov et al. |
| 2014/0219062 | A1* | 8/2014 | Rothberg .............. B81B 7/0077 367/135 |
| 2014/0309503 | A1* | 10/2014 | Arneson .............. A61N 1/0551 600/302 |
| 2015/0032002 | A1* | 1/2015 | Rothberg ............. A61B 8/4488 600/440 |
| 2015/0112233 | A1 | 4/2015 | Towe et al. |
| 2016/0051228 | A1* | 2/2016 | Nakai .................. A61B 5/0095 600/472 |
| 2016/0157717 | A1 | 6/2016 | Gaster |
| 2016/0207760 | A1 | 7/2016 | Rothberg et al. |
| 2016/0303402 | A1* | 10/2016 | Tyler .................... A61N 5/0622 |

OTHER PUBLICATIONS

Denisov et al., "Ultrasonic vs Inductive Power Delivery for Miniature Biomedical Implants," 2010 International Conference on Body Sensor Networks, IEEE Computer Society, pp. 84-89 (Jun. 7-9, 2010).

Eggers et al., "Advanced Hybrid Integrated Low-Power Telemetric Pressure Monitoring System for Biomedical Applications," in The Thirteenth Annual International Conference on Micro Electro Mechanical Systems, MEMS 2000, pp. 329-334.

Harrison et al., "A Low-Power Integrated Circuit for a Wireless 100-Electrode Neural Recording System," IEEE Journal of Solid-State Circuits, 42(1):123-133 (2007).

Harrison et al., "A Low-Power, Low-Noise CMOS Amplifier for Neural Recording Applications," IEEE Journal of Solid-State Circuits, 38(6):958-965 (2003).

International Search Report dated Jan. 5, 2017 in International Application No. PCT/US16/50165.

International Search Report and Written Opinion dated Mar. 13, 2018 in International Application No. PCT/US17/68528.

Jackson et al., "Flexible-CMOS and biocompatible piezoelectric AlN material for MEMS applications," Smart Materials and Structures 22:115033 (2013).

Kim et al., "CMOS Ultrasound Transceiver Chip for High-Resolution Ultrasonic Imaging Systems," IEEE Transactions on Biomedical Circuits and Systems 3(5):293-303 (2009).

Kim et al., "Flexible and Stretchable Electronics for Biointegrated Devices," Annual Review of Biomedical Engineering 14:113-128 (2012).

Kocer et al., "A New Transponder Architecture with On-Chip ADC for Long-Range Telemetry Applications," IEEE Journal of Solid-State Circuits, 41(5):1142-1148 (2006).

Lu et al., "Ultrasonic fingerprint sensor using a piezoelectric micromachined ultrasonic transducer array integrated with complementary metal oxide semiconductor electronics," Applied Physics Letters 106(26):263503 (2015).

Misri et al., "Microfabrication of bulk PZT transducers by dry film photolithography and micro powder blasting," Journal of Micromechanics and Microengineering 22:085017 (2012).

Samaun et al., "An IC Piezoresistive Pressure Sensor for Biomedical Instrumentation," IEEE Transactions on Biomedical Engineering, BME-20(2):101-109 (1973).

Schwiebert et al., "Research Challenges in Wireless Networks of Biomedical Sensors," ACM, 2001 (15 pages).

Shrivastava, Analysis and Design of a 3-stage Voltage Rectifier Multiplier and 2-stage Multi-Phase Voltage Doubler for an Energy Harvesting System. A Thesis. Texas Tech University, Aug. 2012.

Stieglitz et al., "Implantable Biomedical Microsystems for Neural Prostheses," IEEE Engineering in Medicine and Biology Magazine, 24(5):58-65 (2005).

Stieglitz et al., "Micromachined, Polyimide-Based Devices for Flexible Neural Interfaces," Biomedical Microdevices 2(4):283-294 (2000).

Sun et al., "Series resonant ZCS-PFM DC-DC converter with multistage rectified voltage multiplier and dual-mode PFM control scheme for medical-use high-voltage X-ray power generator," IEE Proceedings—Electric Power Applications, 147(6):527-534 (2000).

Tyler et al., "Remote Excitation of Neuronal Circuits Using Low-Intensity, Low-Frequency Ultrasound," PLoS ONE 3(10):e3511 (2008).

Wong et al., "A Very Low-Power CMOS Mixed-Signal IC for Implantable Pacemaker Applications," IEEE Journal of Solid-State Circuits, 39(12):2446-2456 (2004).

\* cited by examiner

MICRON-SCALE ULTRASOUND IDENTIFICATION SENSING TAGS

CROSS-REFERENCE TO RELATED APPLICATIONS

This application is a continuation of International Patent Application No.: PCT/US2016/050165 filed Sep. 2, 2016, which claims priority to U.S. Provisional Application Ser. No. 62/214,822, filed on Sep. 4, 2015, the entire contents of which is incorporated by reference herein.

BACKGROUND

Implantable and injectable electronic devices containing integrated circuit (IC) chips can aid, monitor, or support the functions of organs and even cells, and can be utilized in diagnosis and treatment of medical conditions when implanted or injected into various organs or cells. The sizes of the implantable and injectable devices can vary as a result of the inclusion of components designed to carry out the device functionalities, including the power sources. Batteries can be used as power supplies for implantable and injectable devices. However, batteries can often be bulkier than the IC chips of the implantable and injectable devices, and can require periodic replacement and recharge, limiting the applicability of those devices. Unlike the battery-based power scheme, wireless power transfer from external energy-emitting sources to the implantable and injectable devices can reduce the device size by removing the battery component.

One technique for wirelessly delivering power across biological tissues to implantable and injectable devices is that of inductive coupling. For example, inductive coupling uses a pair of antennas by which power can be transferred across biological tissues via electromagnetic (EM) waves generated from a mutual-inductively coupled link. While attractive when the distance between this pair of antennas is small, the antenna size can be larger than the sizes of the device IC chips. Additionally, certain tissue attenuation of EM waves and the drop of power transfer efficiency when the distance between antennas increases can limit the amount of delivered power and therefore the performances of implantable or injectable devices powered by inductive coupling.

Accordingly, there is a need for improved devices and techniques for wirelessly powering implantable and injectable devices.

SUMMARY

The presently disclosed subject matter provides devices and techniques which integrate piezoelectric transducers, such as polyvinylidene fluoride (PVDF) or lead zirconate titanate (PZT), with customized IC chips to form electronic devices that can be implanted or injected into organs/cells. These implantable and injectable devices can be wirelessly powered by ultrasound waves and can wirelessly transmit data also through ultrasound, therefore referred to as ultrasound identification (USID) sensing tags. The ultrasound waves can have a frequency from 1 MHz-50 MHz, depending on the size of the tag, and can be generated from certain commercial ultrasound imaging equipment, such as, for example and without limitation, the Verasonics Vantage 256 system.

Ultrasound can provide improved power transfer efficiency through biological tissues and enables much smaller device size due to a much smaller wavelength compared to certain other wireless power transfer techniques. For example and without limitation, the wavelength of EM waves at 40 MHz are a few meters in biological tissues, while the wavelength of ultrasound at 40 MHz is approximately 37.5 µm, which is orders of magnitude smaller than that of EM waves at the same frequency.

In an exemplary embodiment, the disclosed subject matter can include tens and even hundreds of micron-scale USID sensing tags implanted or injected into organs/cells of interest. Each individual tag can include a customized IC chip with a piezoelectric transducer integrated on the top surface of the chip. In some embodiments, the IC chips can be formed using a conventional complementary metal-oxide-semiconductor (CMOS) process. The CMOS process can be either a silicon-on-insulator (SOI) CMOS process or a bulk CMOS process. Each individual IC chip can be designed to have a length by width of 150 µm by 150 µm (although different sizes depending on the wavelength of the ultrasound can be used), and multiple IC chips can be contained in a single die. The die thickness can be approximately 300 µm in conventional CMOS processes.

Die/chip thinning processes with a sequential combination of mechanical grinding followed by deep reactive-ion etching (DRIE) can be utilized to reduce the die thickness to approximately 20 µm. The reduced die thickness not only largely decreases the overall device size of the USID sensing tags for various implantation/injection applications, but also reduces the mechanical loading effects on the piezoelectricity of the integrated piezoelectric transducer. Additionally, the integrated piezoelectric transducers can have a length by width by thickness of approximately 150 µm by 95 µm by 28 µm. In such a way, the USID sensing tags can have a size of approximately 150 µm by 150 µm by 48 µm, therefore referred to as "micron-scale."

When excited emitted energy, such as from, commercial ultrasound imaging equipment, an implanted or injected USID sensing tag can reflect part of the received ultrasound waves as echoes back to the equipment, which can form a brightness-mode (B-mode) ultrasound image showing the shape, location, and even movement of the tag. The level of acoustic impedance mismatch between the tag and the surrounding tissues can determine the amplitude of the returned echo signal, which then can determine the brightness of the tag in the ultrasound image.

When receiving ultrasound waves from the ultrasound imaging equipment, the herein disclosed piezoelectric transducer of a USID sensing tag can convert mechanical vibrations of ultrasound waves into electrical energy in the alternating-current (AC) form to provide power for the IC chip. Additionally, the herein disclosed IC chip of a USID sensing tag can include a front-end charge pump, a relaxation oscillator, and a modulator. The charge pump can convert the AC electrical energy generated in the integrated piezoelectric transducer into a direct-current (DC) supply to power the relaxation oscillator. The relaxation oscillator can generate a sub-10-Hz oscillation to drive the modulator.

The modulator can actively modulate the input impedance of the IC chip to cause a periodic impedance change seen by the piezoelectric transducer. This periodic change in input impedance can cause a periodic change in the acoustic impedance mismatch between the tag and the surrounding tissues and therefore the reflectivity of ultrasound waves, or the amount of returned echo signal to form a B-mode image in the ultrasound imaging equipment. This can cause a periodic brightness change of the USID sensing tag in the image and can indicate the powering and detection of the tag. Additional circuitry can be added and configured for sensing functionality with transduced voltages analog-to-digital-converted with a voltage-controlled oscillator, such that, for example and without limitation, changes in voltage can produce discernible changes in oscillation frequency of the backscattered ultrasound energy. Exemplary functionalities can include real-time pH sensing, drug delivery and controlled release, chemical and biological activity detection, and digestion monitoring of small animals.

It is to be understood that both the foregoing general description and the following detailed description are exemplary and are intended to provide further explanation of the disclosed subject matter claimed.

The accompanying figures, where like reference numerals refer to identical or functionally similar elements throughout separate views, serve to further illustrate various embodiments and to explain various principles and advantages all in accordance with the disclosed subject matter. For purpose of explanation and illustration, and not limitation, exemplary aspects and embodiments of the device are shown in FIGS. 1-7.

DETAILED DESCRIPTION

The presently disclosed subject matter provides micron-scale implantable and injectable USID sensing tags, where certain IC chips are integrated with piezoelectric transducers. The USID sensing tags can be wirelessly powered and detected/imaged by ultrasound waves at 1-50 MHz from certain commercial ultrasound imaging equipment. The IC chips can be implemented in conventional CMOS processes and can be fabricated in commercial foundries. The USID sensing tags can be fabricated by integrating the piezoelectric transducers with the IC chips using a series of fabrication processes.

Figure 1:
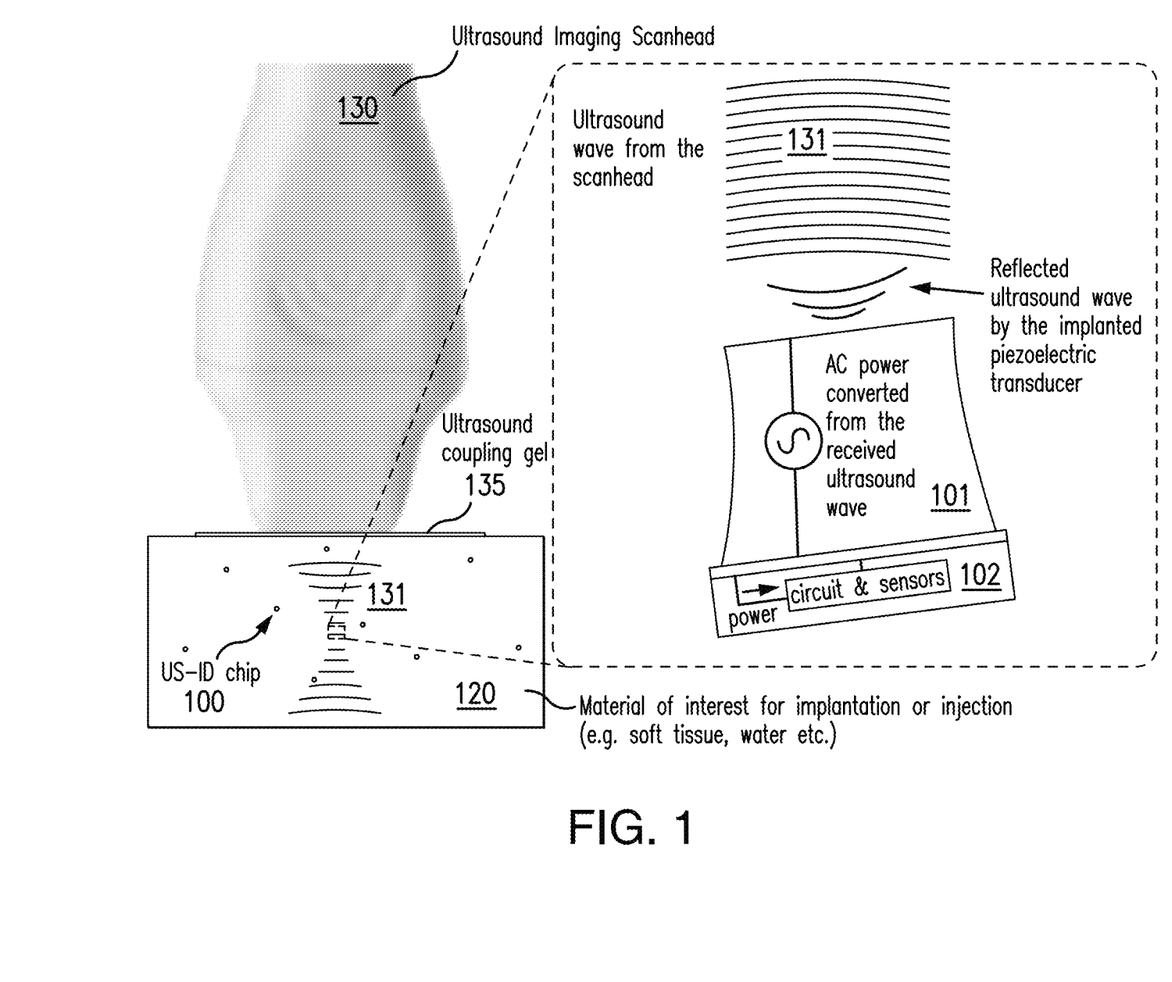
FIG. 1 depicts the operation of multiple USID sensing tags in the organ/cell of interest in accordance with an exemplary embodiment of the disclosed subject matter.

For the purpose of illustration and not limitation, reference is made to the exemplary USID sensing tag 100 shown in exemplary FIG. 1. FIG. 1 illustrates the general operation of the presently disclosed subject matter. For example, the fabricated USID sensing tag 100 can be implanted or injected into a material of interest 120, such as an organ, a cell, soft tissue, or water. The scanhead 130 of commercial ultrasound imaging equipment, such as for example, the Verasonics Vantage 256 system, transmits ultrasound waves 131 to the USID sensing tag 100 through the material of interest 120. Additionally or alternatively, and as shown in exemplary FIG. 1, an ultrasound coupling gel 135 can be applied in between the scanhead 130 and the surface of the material of interest 120 to improve the transmission of ultrasound waves 131 from the scanhead 130 to the USID sensing tag 100. The ultrasound coupling gel 135 can, for example, improve transmission of ultrasound waves 131 since ultrasound waves 131 can exhibit inferior transmission through air than through the ultrasound coupling gel 135. The mechanical energy of the ultrasound waves 131 of exemplary FIG. 1 can be converted to electrical energy by the piezoelectric transducer 101 integrated onto the IC chip 102 of the USID sensing tag 100. The electrical energy converted from ultrasound waves 131 can power the IC chip 102 for sensing and data transmission.

Further to the above, the disclosed subject matter can include a method for fabricating the USID sensing tags, which can include, for example and without limitation, thinning and surface planarization of the die that contains the IC chips, separation of individual IC chips on the die, passivation of the individual IC chips for biocompatibility, integration of the individual IC chips with their corresponding piezoelectric transducers, and release of the resulting devices from the die. For example, a die that contains the IC chips can be thinned from a thickness of approximately 300 µm down to a thickness of approximately 20 µm, which renders the originally brittle die thin and flexible. Exemplary techniques for thinning chip die can include a sequential combination of mechanical grinding followed by DRIE (deep reactive-ion etching). Other suitable thinning techniques are also within the scope of the presently disclosed subject matter.

For example and without limitation, a method of fabricating the USID sensing tags is illustrated in exemplary FIGS. 2A-2I. As shown in exemplary FIG. 2A, the thinned IC die 201 can be placed on top of a backing layer made of aluminum for mechanical support and then transferred onto a carrier substrate for convenient handling during the subsequent fabrication processes. The carrier substrates can be, for example, materials capable of withstanding the subsequent fabrication processes, such as a semiconductor wafer or glass. Between exemplary FIGS. 2A to 2B, the top surface 211 of the die 201 containing the IC chips is planarized by uniformly etching the passivation layer using reactive-ion etching (RIE).

Figure 2A:
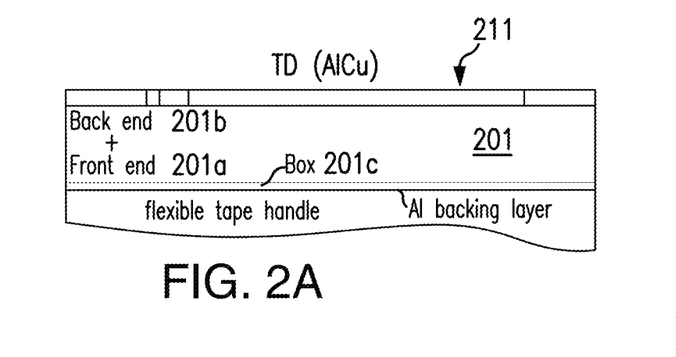
FIGS. 2A-2I depict a fabrication process for producing the USID sensing tags in accordance with an exemplary embodiment of the disclosed subject matter.
Figure 2B:
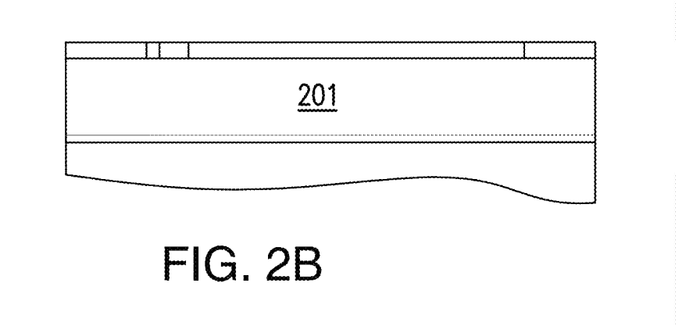
Figure 2C:
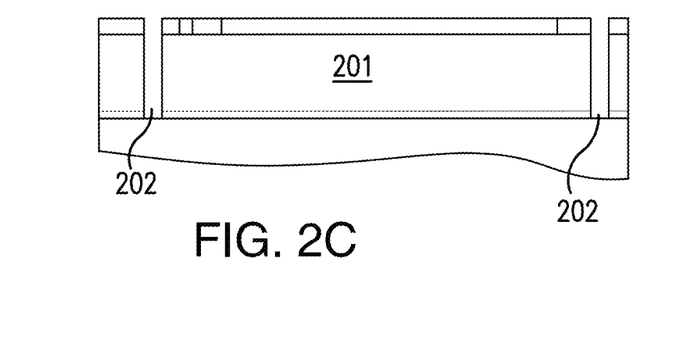
Figure 2D:
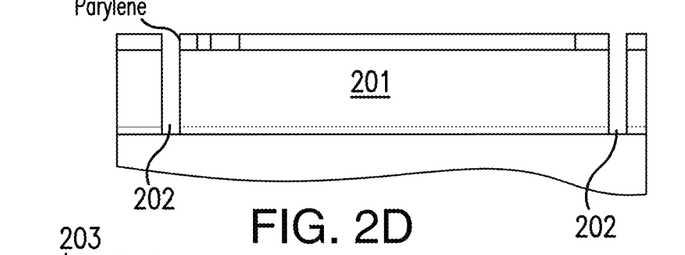

Next, as shown in exemplary FIG. 2C, the individual IC chips on the die 201 are separated by performing dry etching in RIE for front-end-of-line (FEOL) 201a, back-end-of-line (BEOL) 201b, and buried oxide (BOX) 201c to form vertical trenches 202 around the active areas of the IC chips. For example and without limitation, the FEOL 201a can refer to the first part of the IC chips that contain individual components, such as transistors, resistors, and capacitors. The BEOL 201b can refer to the second part of IC chips where these individual components get interconnected with metalization layers. The BOX 201c can refer to an insulator layer made of oxide and buried in the silicon wafer of SOI CMOS processes. As shown in exemplary FIG. 2D, the sidewalls of the IC chips in their respective vertical trenches 202 can be passivated. Passivation of the sidewalls can include for example, depositing conformal parylene to fill the vertical trenches 202 thereto to permit biocompatibility of the IC chips with biological tissues.

Figure 2E:
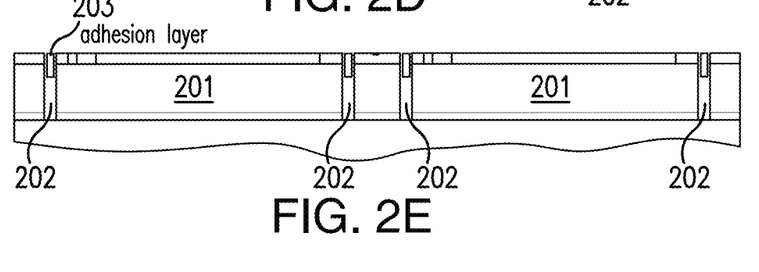
Figure 2F:
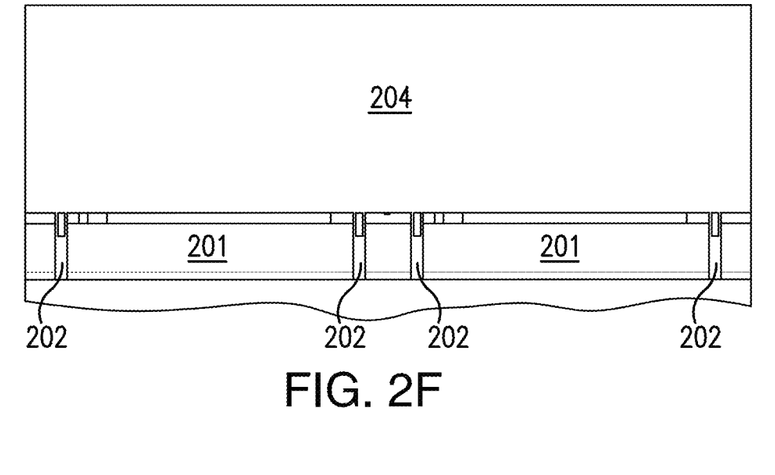

An anisotropic conductive adhesive can then be deposited onto the surface 211 of the IC chips, as illustrated in exemplary FIG. 2E. For example and without limitation, the adhesion material selected and deposited can conduct vertically only and not laterally in order to avoid shorting adjacent pads/electrodes. Following the deposition of the adhesion layer 203, the fabrication process of the presently disclosed subject matter can include integrating piezoelectric transducers onto the IC chips. Such integration is illustrated in exemplary FIG. 2F. Each individual IC chip contains an input pad and a ground pad, and a piezoelectric transducer has a top electrode and a bottom electrode between which the electrical energy converted from the incoming ultrasound waves is produced. The integration of a piezoelectric transducer with an IC chip can include the electrical connections of the bottom transducer electrode with the chip input pad and the top transducer electrode with the chip ground pad. For example and without limitation, a piece of piezoelectric transducer 204 that completely covers the top surface 211 of the die 201 containing the IC chips can be placed on top of the adhesion layer 203 to make the electrical connection between the input pads of the IC chips and the corresponding bottom transducer electrodes.

Figure 2G:
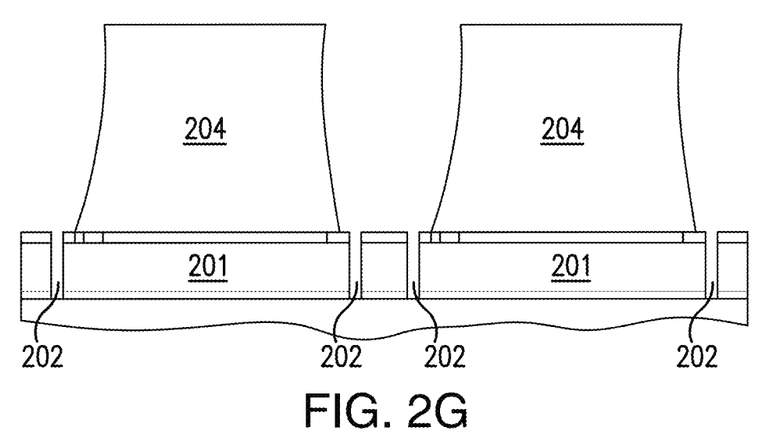
Figure 2H:
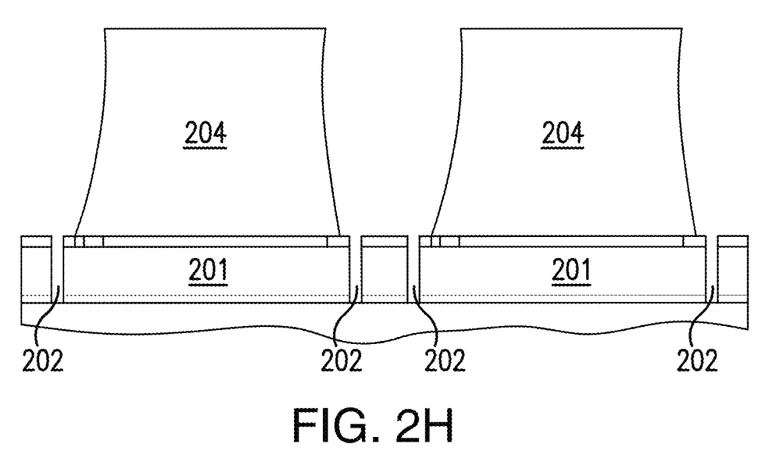
Figure 2I:
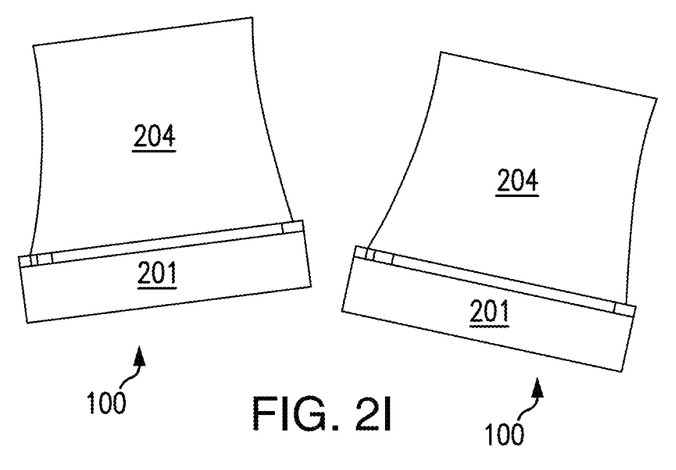

As shown in exemplary FIG. 2G, the piezoelectric transducer 204 is then patterned with the AZ4620 photoresist as an etch mask and subsequently etched in RIE to expose the ground pads of the IC chips. Other suitable patterning techniques are also within the scope of the presently disclosed subject matter. The top transducer electrodes can then be electrically connected to the chip ground pads via deposition of titanium metal for biocompatibility, followed by a lift-off process to remove unwanted metallization, as illustrated in exemplary FIG. 2H. The fabricated devices 100 can be released from the carrier substrate by selectively etching away the backing layer, as illustrated in exemplary FIG. 2I. The released devices can be transferred to deionized water for rinsing. Such fully fabricated USID sensing tags 100 can be either dried or can be implanted/injected into a sample of interest using a syringe.

Figure 3:
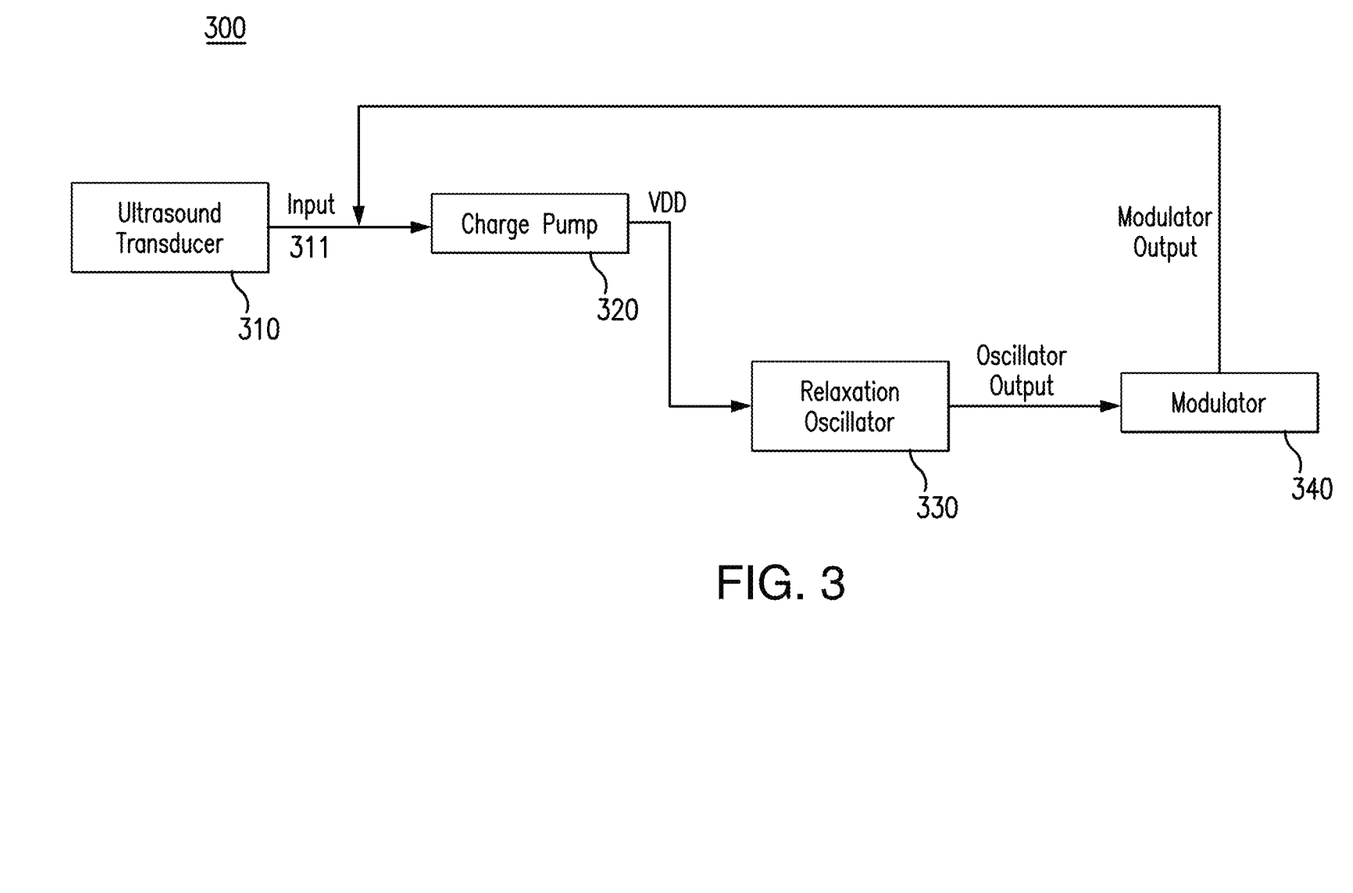
FIG. 3 depicts a circuit block diagram in accordance with an exemplary embodiment of the disclosed subject matter.

As disclosed herein, and with reference to exemplary FIG. 3, the USID sensing tag can include an IC chip configured in accordance with the disclosure herein. For example and without limitation, the IC chip herein disclosed and illustrated in exemplary FIG. 3 can be implemented in a 180-nm CMOS technology provided by Taiwan Semiconductor Manufacturing Company (TSMC). An exemplary overall circuit block diagram 300 of the IC chip is depicted by way of example and explanation only, and not limitation. The customized IC chip can include a front-end charge pump 320, coupled to receive the AC input signal 311 from the integrated piezoelectric transducer 310 and is configured to produce a DC output. The IC chip further includes a relaxation oscillator 330, coupled to the charge pump 320. The relaxation oscillator 330 can be configured to receive power from the DC output generated in the charge pump 320 and produce a periodic oscillation signal. The IC chip further includes a modulator 340, coupled to the relaxation oscillator 330. The modulator can be configured to receive the oscillation signal from the relaxation oscillator and accordingly modulate the input impedance of the IC chip.

Figure 4:
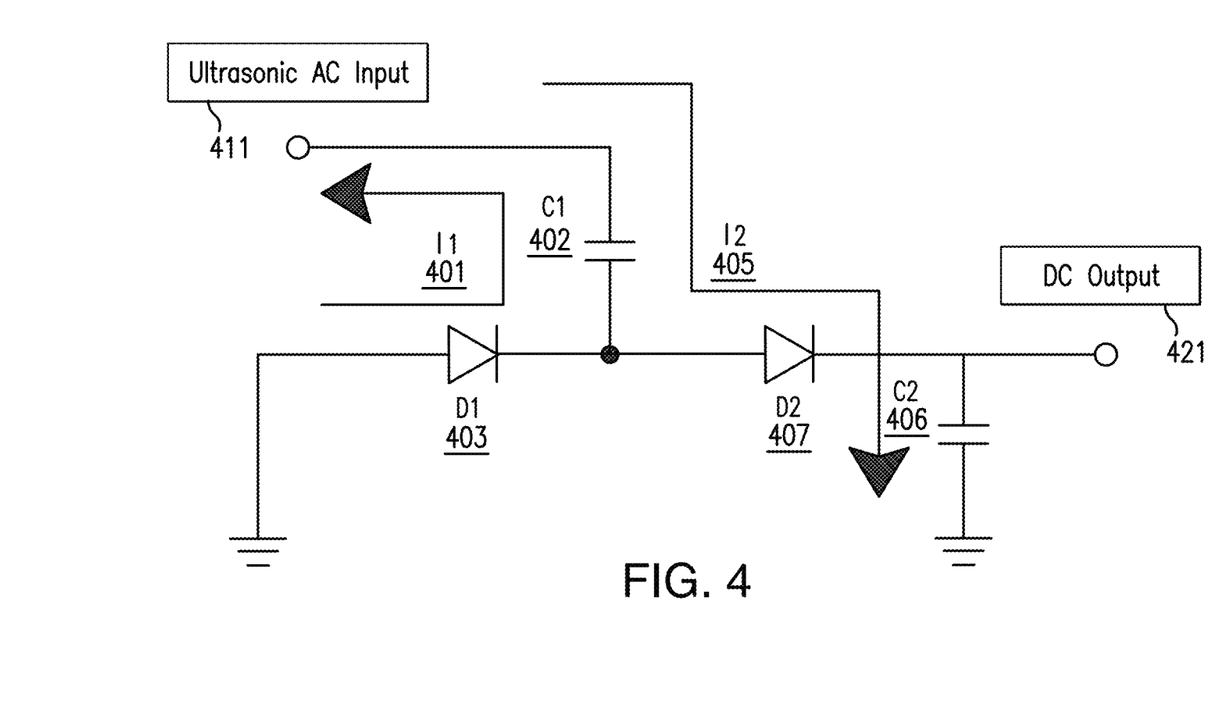
FIG. 4 depicts a circuit schematic diagram in accordance with an exemplary embodiment of the disclosed subject matter.

The front-end charge pump 320 can be configured to convert the input AC signal into a DC voltage to power the relaxation oscillator 330 as shown in exemplary FIG. 3. A circuit diagram for the charge pump is provided in FIG. 4. When the AC input 411 from the piezoelectric transducer is negative, the current $I_1$ 401 charges $C_1$ 402 to the peak value of the input through $D_1$ 403; when the input is positive, in addition to the existing voltage across $C_1$ 402, the current $I_2$ 405 charges $C_2$ 406 to double the peak voltage of the input through $D_2$ 407, creating a voltage that is twice the peak valve of the AC input 411 at the DC output 421. Additionally or alternatively, $C_2$ 406 can also be used as a storage capacitor to store the energy accumulated from the input source.

Figure 5:
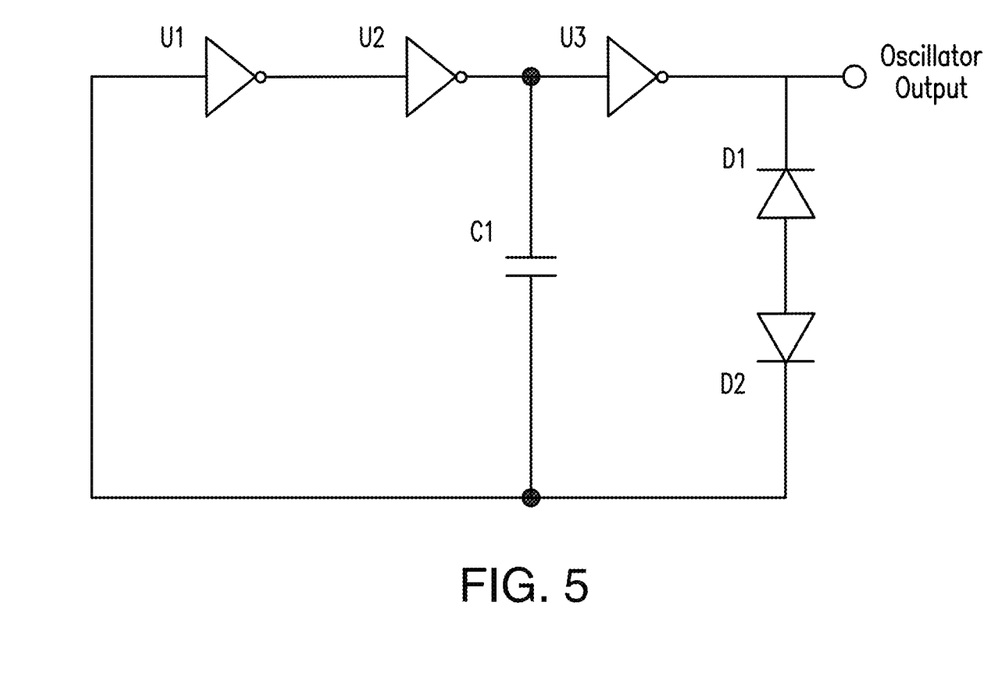
FIG. 5 depicts a circuit schematic diagram in accordance with an exemplary embodiment of the disclosed subject matter.

A circuit diagram for the relaxation oscillator 330, with reference to exemplary FIG. 3, is provided in FIG. 5. The relaxation oscillator 330 of the presently disclosed subject matter can include three inverters, $U_1$, $U_2$ and $U_3$, a capacitor $C_1$ and a resistor as illustrated by way of example in FIG. 5. Such circuitry can be configured to produce a specific oscillation frequency depending on the value of the capacitor and resistor. Additionally, the resistor in the oscillator of exemplary FIG. 5 can be implemented using the cathodes of two diodes $D_1$ and $D_2$ connected in series. These diodes can provide a high resistance on the order of hundreds of Giga Ohms (G$\Omega$), and therefore can produce an oscillation frequency of a few Hz. The measured oscillation frequency of the present oscillator is approximately 1.8 Hz and measured power consumption is 3.24 nW.

Figure 6:
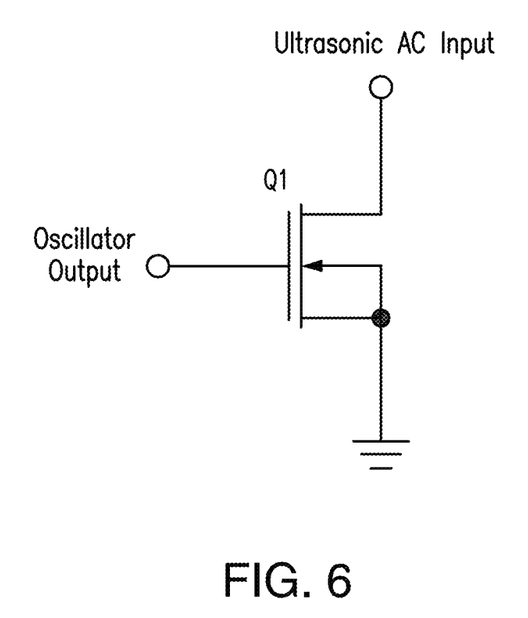
FIG. 6 depicts a circuit schematic diagram in accordance with an exemplary embodiment of the disclosed subject matter.

With reference to exemplary FIG. 3, a modulator 340 can be configured to actively modulate the input impedance of the IC chip. As illustrated in exemplary FIG. 6, the modulator 340 can include a single n-channel metal-oxide-semiconductor field-effect transistor (MOSFET) $Q_1$. The MOSFET includes at least three terminals, including a gate, a source, and a drain, where the gate is connected to and controlled by the output of the relaxation oscillator 330, the source is connected to ground and the drain is connected to the ultrasonic AC input 311. Such configuration can cause the input impedance of the USID sensing tag to appear as solely the piezoelectric transducer 310 when the oscillator output is in the low state and as a parallel combination of the piezoelectric transducer 310 and the capacitance between the drain and source of the MOSFET when the oscillator output is in the high state. The modulator 340 of exemplary FIG. 3 is thereby implementing a standard amplitude-shift keying (ASK) scheme to alter the echo reflected from the piezoelectric transducer 310 during excitation. For example and without limitation, the size of the MOSFET can be 2 μm/450 nm (length/width) so that the impedance at the ultrasonic input 311 can be decreased by a factor of approximately three when the oscillator output changes from the low state to the high state, thereby modulating the reflected ultrasound waves back to the ultrasound imaging equipment. By way of example only, and not limitation, the B-mode ultrasound image scan can be used to confirm the functionality of the presently disclosed subject matter. When a USID sensing tag is functional upon excitation, the tag appears as a blinking dot in the ultrasound image as its brightness periodically changes according to the modulation of the reflected ultrasound echo signals back to the imaging equipment.

Figure 7:
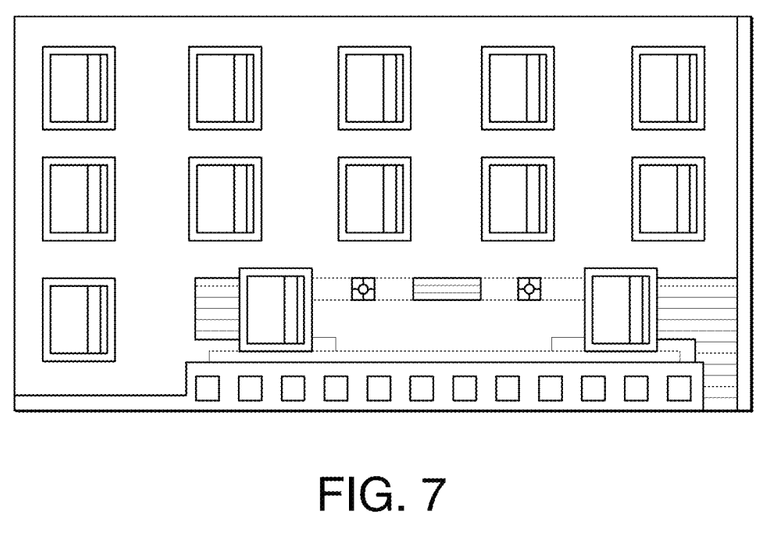
FIG. 7 depicts a die diagram in accordance with an exemplary embodiment of the disclosed subject matter.

Exemplary FIG. 7 shows a diagram of the die containing the IC chips implemented in a 180-nm CMOS technology provided by TSMC.

As herein disclosed, the commercial ultrasound imaging equipment utilized to provide ultrasound waves to the USID sensing tags can be designed for medical imaging of small animals in a preclinical setting, including, but not limited to, cardiac, vascular, tumor and molecular imaging for mouse, rat, rabbit and zebra fish. Additionally, the size and power requirement of the micron-scale USID sensing tags matches the spatial resolution and energy intensity of the ultrasound waves in the chosen 30 MHz-50 MHz range from the imaging equipment. Also, the USID sensing tags can potentially incorporate sensors for in-vivo acquisition of various physiological signals. Therefore, the USID sensing tags of the presently disclosed subject matter can be implanted or injected into various organs in several kinds of small animals and excited/imaged by the commercial ultrasound imaging equipment for numerous applications and studies. With different kinds of embedded sensors, applications of these tags include, but not limited to, monitoring electrophysiology in the brain through the vasculature, probing intracellular activities by examining concentrations of certain molecules, and detecting biogenic amine levels in the gastrointestinal tract to study communication between the microbiota and the brain.

The description herein merely illustrates the principles of the disclosed subject matter. Various modifications and alterations to the described embodiments will be apparent to those skilled in the art in view of the teachings herein. Accordingly, the disclosure herein is intended to be illustrative, but not limiting, of the scope of the disclosed subject matter. Moreover, the principles of the disclosed subject matter can be implemented in various configurations of hardware, and are not intended to be limited in any way to the specific embodiments presented herein.

The invention claimed is:

1. An ultrasound identification sensing tag powered by ultrasound signals from commercial ultrasound imaging equipment, comprising:
   a piezoelectric transducer configured to convert mechanical energy of said ultrasound signals into alternating-current (AC) electrical energy; and
   an integrated circuit chip, electrically coupled to said piezoelectric transducer, comprising:
   (i) circuitry configured to at least receive said electrical energy for power and to actively modulate an input impedance of the integrated circuit chip, and
   (ii) a relaxation oscillator, coupled to a charge pump, and configured to receive a DC output voltage from said charge pump and generate an oscillation signal, and wherein said relaxation oscillator comprises three inverters, one capacitor, and two diodes,
   wherein said integrated circuit chip and said piezoelectric transducer are integrated.

2. The ultrasound identification sensing tag of claim 1, wherein said ultrasound signals from said commercial ultrasound imaging equipment comprise ultrasound waves within a range of 1 MHz to 50 MHz.

3. The ultrasound identification sensing tag of claim 1, wherein said integrated circuit chip is passivated by parylene.

4. The ultrasound identification tag of claim 1, wherein said piezoelectric transducer includes at least one of polyvinylidene fluoride (PVDF) or lead zirconate titanate (PZT).

5. The ultrasound identification sensing tag of claim 1, wherein said integrated circuit chip further comprises:
   the charge pump, coupled to receive said AC electrical energy from said piezoelectric transducer, configured to produce a direct-current (DC) output voltage;
   a modulator, coupled to said relaxation oscillator, configured to receive said oscillation signal from said relaxation oscillator and modulate said input impedance of said integrated circuit chip.

6. The ultrasound identification sensing tag of claim 5, wherein said charge pump further comprises two capacitors and two diodes.

7. The ultrasound identification sensing tag of claim 5, wherein said modulator further comprises an n-channel metal-oxide-semiconductor field-effect transistor (MOSFET) having a gate, said gate being controlled by said oscillation signal.

8. The ultrasound identification sensing tag of claim 5, wherein said modulator is further configured to actively modulate said input impedance of said integrated circuit chip to cause a periodic impedance change seen by said piezoelectric transducer, said periodic impedance change being detectable by said piezoelectric transducer.

9. The ultrasound identification sensing tag of claim 8, wherein said periodic impedance change detectable by said piezoelectric transducer causes a periodic change in an acoustic impedance mismatch between said ultrasound identification sensing tag and one or more surrounding tissues, said acoustic impedance mismatch creating an echo signal transmitted from said piezoelectric transducer and returned back to said commercial ultrasound imaging equipment; wherein said echo signal forms a brightness-mode (B-mode) image in said commercial ultrasound imaging equipment and causes a periodic brightness change of said ultrasound identification sensing tag in said brightness-mode (B-mode) image, indicating said ultrasound identification sensing tag is functional.

10. The ultrasound identification sensing tag of claim 1, wherein said ultrasound identification sensing tag further comprises sensors for receiving one or more physiological signals from a biological tissue to enable applications including at least one of real-time pH sensing, drug delivery and controlled release, chemical and biological activity detection, and digestion monitoring.

11. The ultrasound identification sensing tag of claim 1, wherein said integrated circuit chip further comprises a modulator coupled to a relaxation oscillator, wherein said modulator is configured to receive an oscillation signal from said relaxation oscillator and actively modulate said input impedance of said integrated circuit chip to cause a periodic impedance change seen by said piezoelectric transducer, said periodic impedance change being detectable by said piezoelectric transducer,
   wherein said periodic impedance change detectable by said piezoelectric transducer causes a periodic change in an acoustic impedance mismatch between said ultrasound identification sensing tag and one or more surrounding tissues, said acoustic impedance mismatch creating an echo signal transmitted from said piezoelectric transducer and returned back to said commercial ultrasound imaging equipment, and
   wherein said echo signal forms a brightness-mode (B-mode) image in said commercial ultrasound imaging equipment and causes a periodic brightness change of said ultrasound identification sensing tag in said brightness-mode (B-mode) image, indicating said ultrasound identification sensing tag is functional.

12. The ultrasound identification sensing tag of claim 1, wherein said integrated circuit chip has a thickness of approximately 20 µm.

13. The ultrasound identification sensing tag of claim 1, wherein said piezoelectric transducer has a length of approximately 150 µm, a width of approximately 95 µm and a thickness of approximately 28 µm.

14. The ultrasound identification sensing tag of claim 1, wherein said ultrasound identification sensing tag has a length of approximately 150 µm, a width of approximately 150 µm and a thickness of approximately 48 µm.

15. The ultrasound identification sensing tag of claim 7, wherein said n-channel MOSFET is a single n-channel MOSFET.

16. The ultrasound identification sensing tag of claim 1, wherein said piezoelectric transducer is integrated on a surface of said integrated circuit chip.

17. An ultrasound identification sensing tag powered by ultrasound signals from commercial ultrasound imaging equipment, comprising:
- a piezoelectric transducer configured to convert mechanical energy of said ultrasound signals into alternating-current (AC) electrical energy; and
- an integrated circuit chip, electrically coupled to said piezoelectric transducer, comprising:
  - (i) circuitry configured to at least receive said electrical energy for power and to actively modulate an input impedance of the integrated circuit chip;
  - (ii) a charge pump, coupled to receive said AC electrical energy from said piezoelectric transducer, configured to produce a direct-current (DC) output voltage;
  - (iii) a relaxation oscillator, coupled to said charge pump, configured to receive said DC output voltage from said charge pump and generate an oscillation signal; and
  - (iv) a modulator, coupled to said relaxation oscillator, configured to (i) receive said oscillation signal from said relaxation oscillator and modulate said input impedance of said integrated circuit chip and (ii) actively modulate said input impedance of said integrated circuit chip to cause a periodic impedance change seen by said piezoelectric transducer, said periodic impedance change being detectable by said piezoelectric transducer,
- wherein said integrated circuit chip and said piezoelectric transducer are integrated, and
- wherein said periodic impedance change detectable by said piezoelectric transducer causes a periodic change in an acoustic impedance mismatch between said ultrasound identification sensing tag and one or more surrounding tissues, said acoustic impedance mismatch creating an echo signal transmitted from said piezoelectric transducer and returned back to said commercial ultrasound imaging equipment; wherein said echo signal forms a brightness-mode (B-mode) image in said commercial ultrasound imaging equipment and causes a periodic brightness change of said ultrasound identification sensing tag in said brightness-mode (B-mode) image, indicating said ultrasound identification sensing tag is functional.

18. An ultrasound identification sensing tag powered by ultrasound signals from commercial ultrasound imaging equipment, comprising:
- a piezoelectric transducer configured to convert mechanical energy of said ultrasound signals into alternating-current (AC) electrical energy; and
- an integrated circuit chip, electrically coupled to said piezoelectric transducer, comprising:
  - (i) circuitry configured to at least receive said electrical energy for power and to actively modulate an input impedance of the integrated circuit chip, and
  - (ii) a modulator coupled to a relaxation oscillator, wherein said modulator is configured to receive an oscillation signal from said relaxation oscillator and actively modulate said input impedance of said integrated circuit chip to cause a periodic impedance change seen by said piezoelectric transducer, said periodic impedance change being detectable by said piezoelectric transducer,
- wherein said periodic impedance change detectable by said piezoelectric transducer causes a periodic change in an acoustic impedance mismatch between said ultrasound identification sensing tag and one or more surrounding tissues, said acoustic impedance mismatch creating an echo signal transmitted from said piezoelectric transducer and returned back to said commercial ultrasound imaging equipment,
- wherein said echo signal forms a brightness-mode (B-mode) image in said commercial ultrasound imaging equipment and causes a periodic brightness change of said ultrasound identification sensing tag in said brightness-mode (B-mode) image, indicating said ultrasound identification sensing tag is functional, and
- wherein said integrated circuit chip and said piezoelectric transducer are integrated.

* * * * *